United States Patent [19]

Rose et al.

[11] Patent Number: 4,605,395

[45] Date of Patent: Aug. 12, 1986

[54] HYDROCEPHALY TREATMENT DEVICE INCLUDING A VARIABLE IMPEDANCE FILTER

[75] Inventors: Christian Sainte Rose; Jacques Lacombe, both of Paris, France

[73] Assignee: Universite Rene Descartes (Paris V), Paris, France

[21] Appl. No.: 570,686

[22] Filed: Jan. 13, 1984

[30] Foreign Application Priority Data

Jan. 14, 1983 [FR] France ................................ 83 00546

[51] Int. Cl.[4] ................................................ A61M 5/00

[52] U.S. Cl. ............................................ 604/9; 604/8

[58] Field of Search ....................................... 604/8–10; 137/512.1, 513.5, 513.7, 519.5; 604/246, 247, 30, 31, 118

[56] References Cited

U.S. PATENT DOCUMENTS

| | | | |
|---|---|---|---|
| 1,011,797 | 12/1911 | Howell | 137/513.5 |
| 2,999,499 | 9/1961 | Willet | 604/80 |
| 3,216,418 | 11/1965 | Scislowicz | 604/80 |
| 3,320,971 | 5/1967 | Hemenway | 137/512.1 |
| 3,758,073 | 9/1973 | Schulte | 604/9 |
| 3,769,982 | 11/1973 | Schulte . | |
| 3,861,415 | 1/1975 | Larsen | 137/513.5 |
| 3,889,687 | 6/1975 | Harris et al. . | |
| 3,894,541 | 7/1975 | El-Shafei . | |
| 3,991,768 | 11/1976 | Portnoy | 604/10 |
| 4,187,874 | 2/1980 | Essebaggers | 137/512.1 |
| 4,443,214 | 4/1984 | Marion | 604/9 |

FOREIGN PATENT DOCUMENTS

| | | | |
|---|---|---|---|
| 0668815 | 1/1983 | European Pat. Off. . | |
| 0442599 | 4/1927 | Fed. Rep. of Germany | 604/247 |
| 0020471 | of 1903 | United Kingdom | 604/30 |

*Primary Examiner*—John D. Yasko

*Assistant Examiner*—Gene B. Kartchner

*Attorney, Agent, or Firm*—Robbins & Laramie

[57] ABSTRACT

To treat hydrocephaly, an intracranial catheter is implanted in the head. It is connected to a tube fitted with a non-return valve and serves to divert the flow of cephalo-rachidian liquid to the peritoneum or to the right auricle of the heart. In accordance with the invention a hydraulic filter of non-linear variable impedance is connected in the tube in series with the valve. The filter maintains an average flow rate of the cephalo-rachidian liquid close to the physiological flow rate, but prevents sudden rushes of fluid flow, thereby permitting the intracranial pressure to vary in the short term in the normal manner over a characteristic period of about one second, while preventing said pressure from rising slowly in the long term, e.g. over a characteristic period of about one minute. This is done by a bead (160) which is housed in a cavity (161) extending between a proximal orifice (111) and a distal orifice (136). The distal orifice constitutes a leaky valve seat for the bead.

12 Claims, 7 Drawing Figures

296A 212 250 239 238 282 255 230 280 270 284 285 211 283 281 231 232 210 261 260 236 235 234 200

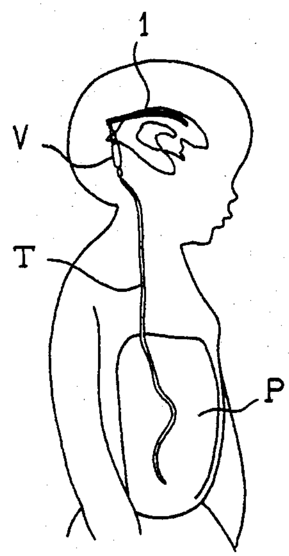
FIG_1A
FIG_1B
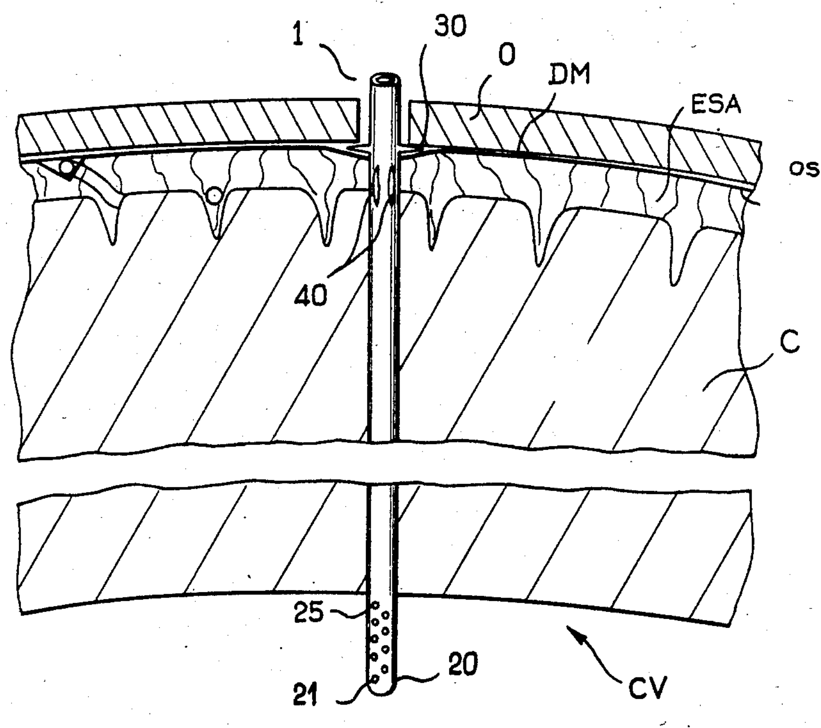
FIG_6

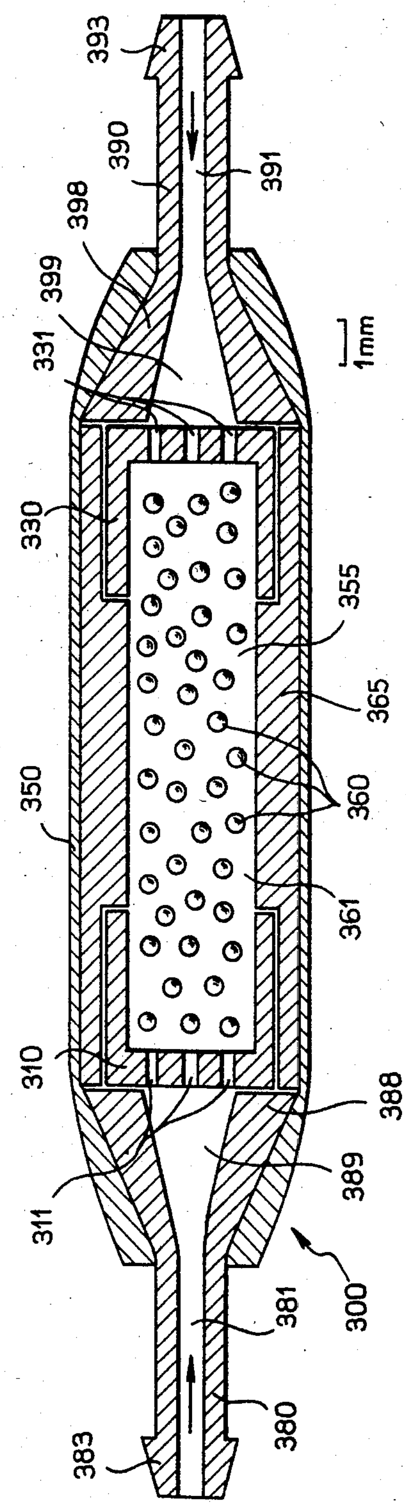
393
390
391
398
399
331
1mm
330
355
365
350
360
361
310
388
389
311
300
381
380
383
FIG_4
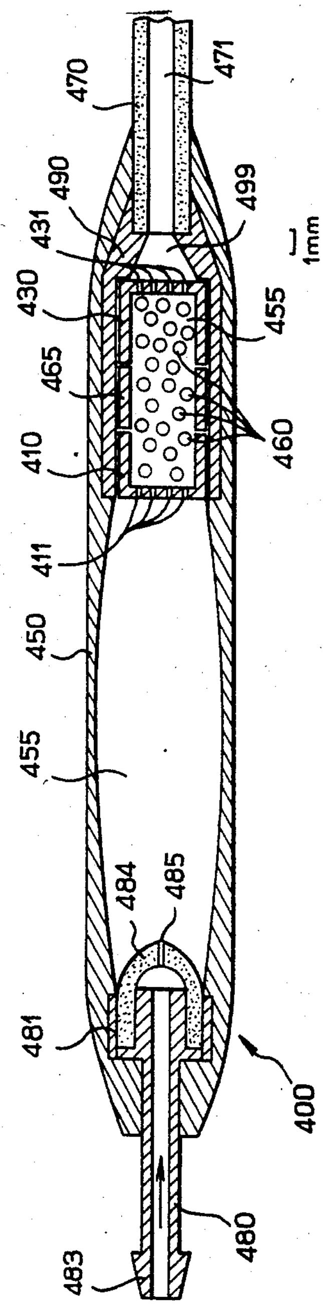
470
471
490
499
431
1mm
430
455
465
460
410
411
450
455
484
485
481
400
480
483
FIG_5

HYDROCEPHALY TREATMENT DEVICE INCLUDING A VARIABLE IMPEDANCE FILTER

The present invention relates to the treatment of hydrocephaly.

BACKGROUND OF THE INVENTION

The hydrocephaly treatment devices currently in use comprise an intracranial catheter connected to a tube which is fitted with a valve and which enables the flow of cephalo-rachidian liquid to be diverted to one or more cavities in the organism capable of absorbing said liquid. As a general rule the cavity used is the peritoneum or the right auricle of the heart.

The valves used over the last 20 years have been based on the principle of maintaining a constant intracranial pressure regardless of the flow rate. Various types of non-return valve opening at a threshold pressure have thus been used, sometimes in conjunction with anti-siphon valves.

These devices do not give entire satisfaction: they clip all variations in intracranial pressure regardless of whether they are abnormal or normal (e.g. when making an effort, or during paradoxical sleep); furthermore, they cope poorly with the suction effects due to sudden pressure drops induced in the tube when the patient rises from a lying position to a sitting position, or from a sitting position to a standing position.

The present invention provides a device which goes against the principle of maintaining the intracranial pressure constant.

SUMMARY OF THE INVENTION

Thus, according to a very general definition of the invention, the treatment device tube includes a hydraulic filter of non-linear variable impedance connected in the tube in series with the valve, said filter maintaining an average flow rate of the cephalo-rachidian liquid close to the physiological flow rate, thereby permitting the intracranial pressure to vary in the short term over a characteristic period of about one second, while preventing the pressure from varying in the long term over a characteristic period of about one minute.

In a preferred embodiment of the invention, the hydraulic filter is placed in the vertical portion of the path of the tube; it includes at least one bead movably lodged on the path of the cephalo-rachidian liquid between a filter inlet orifice and a filter outlet orifice both of smaller diameter than the bead; the outlet orifice together with the bead forming the seat of a leakage rate valve, thereby defining the abovementioned average flow rate.

Typically the fluid flow rate is about 8 $cm^3$ to 30 $cm^3$ per hour for a static pressure difference of 5 cm to 40 cm of water across the filter.

Such a hydraulic filter may advantageously be incorporated in a common structure with a non-return valve which opens at a fixed threshold pressure.

In a first specific embodiment of the invention the filter includes a single bead and the filter outlet orifice has its surface so shaped as to form a leak-defining seat of a leakage rate valve. The bead is about 2 millimeters (mm) in diameter.

In another specific embodiment, the filter includes a large number of microbeads, with the inlet and outlet orifices being formed by filters having perforations of smaller width than the diameter of the microbeads.

Preferably, the microbeads have a diameter of 0.1 mm to 0.6 mm. In practice, they occupy 50% to 90% of the inside volume of the chamber in which they are lodged between the inlet and the outlet orifices.

The filter of the present invention combines readily with an intracranial catheter which includes a positioning protuberance or stop member at a predetermined distance from a free end of the catheter having orifices for communicating with cerebral ventricles, and which further includes one or more intermediate orifices close to the protuberance on its free end side for communicating with the sub-arachnoid spaces of the cranial cavity, thereby making it possible to avoid inverting the pressure gradient between the ventricular cavities and the periphery of the cerebral parenchyma.

BRIEF DESCRIPTION OF THE DRAWINGS

Embodiments of the invention are described by way of example with reference to the accompanying drawings, in which:

FIGS. 1A and 1B are very diagrammatic illustrations of hydrocephaly treatment by diverting liquid to the peritoneum and to the right auricle of the heart respectively;

FIG. 4 is a longitudinal section through a second embodiment of a filter in accordance with the invention;

FIG. 5 is a similar view to FIG. 4, but showing a variant in which the filter is incorporated in a valve; and FIG. 6 shows an improved catheter which is preferred for use in a device in accordance with the invention.

MORE DETAILED DESCRIPTION

FIG. 1A shows an intracranial catheter 1 connected to the peritoneal cavity P of a hydrocephalic child by means of a tube T including a valve V. FIG. 1B shows a similar arrangement, but leading to the right auricle of the heart A.

These devices for treating hydrocephaly are practically the only ones currently in use after trials in numerous directions. However, they still pose problems, of which the most severe are complications associated with sub-dural hematoma. The cause is usually excessive drainage of cephalo-rachidian liquid from the cerebral ventricles. This phenomenon cannot be completely avoided by non-return valves opening at a threshold pressure, even when associated with an anti-siphon valve.

Further, such threshold pressure valves have the effect of maintaining the intracranial pressure at a constant value regardless of the rate at which the cephalo-rachidian liquid is flowing. However, this has the effect of clipping all variations, including normal variations, in the intracranial pressure. The following normal variations in intracranial pressure have been observed:

a permanent background of low-amplitude, short-term variations related to the pulse and to breathing;

during paradoxical sleep, somewhat erratic, longer-term, and greater-amplitude variations are superposed thereon; and during wakefulness, fairly regular, likewise longer-term, and medium amplitude variations are superposed on the said background.

The interactions which give rise to these variations in pressure are poorly understood: a complete explanation for the variations in intracranial pressure observed during paradoxical sleep is not yet available. However, clipping such variations by means of a pressure threshold valve goes against the normal physiological state of affairs.

Under such conditions the aim of the present invention is to provide a hydrocephaly treatment device which operates in a manner which is closer to normal physiology.

To this end, a special filter (see FIG. 2 or FIG. 4) is inserted in the vertical path of the tube T either upstream or downstream of the valve V. Alternatively, the filter may be incorporated in the valve, as shown in FIGS. 3 and 5.

A first, single-bead, embodiment of the invention is initially described with reference to FIGS. 2 and 3.

Figure 2:
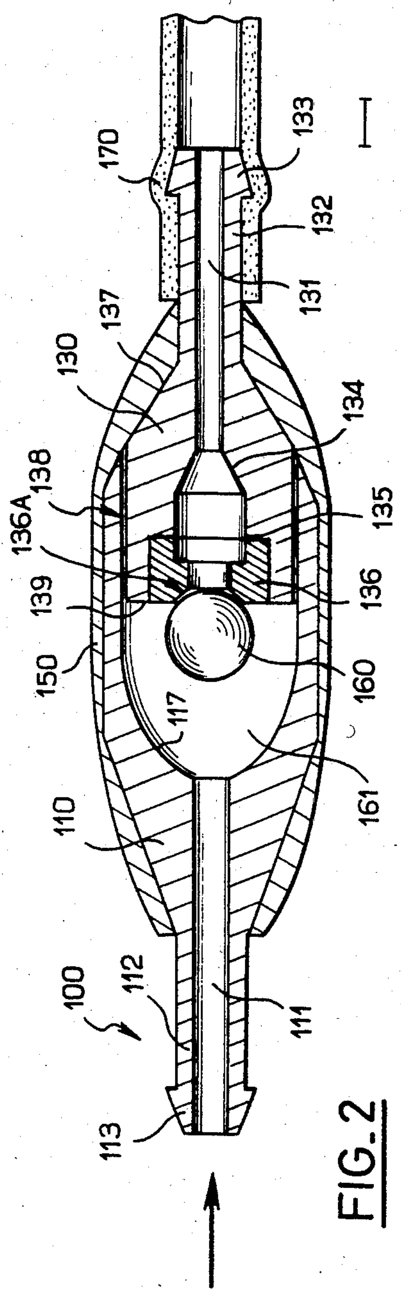
FIG. 2 is a longitudinal section through a first embodiment of a filter in accordance with the invention.
Figure 3:
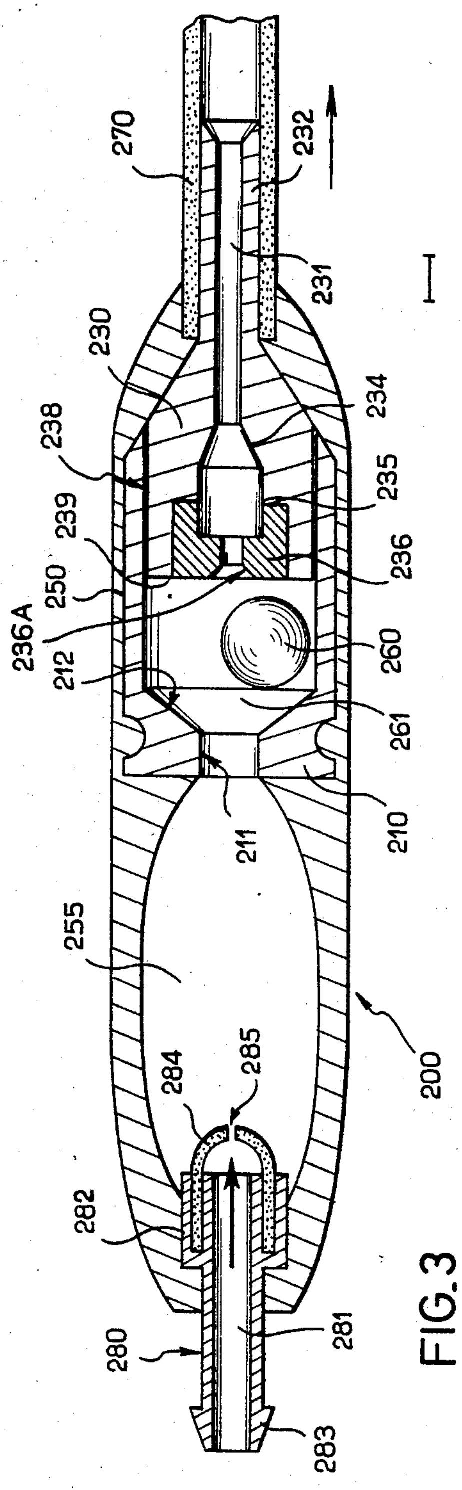
FIG. 3 is a similar view to FIG. 2, but showing a variant in which the filter is incorporated in a valve.

FIG. 2 shows a filter having an overall reference 100. It comprises two main body members 110 and 113 which are glued together over a cylindrical surface 138. The lefthand side of the figure corresponds to the upstream end of the filter. The body member 110 has an inlet tube 112 projecting therefrom with a bore 111 and a fixing nose 113 at the end thereof. The bore 111 opens out into the apex of a domed and generally paraboloidal surface 117 which runs smoothly into the cylindrical surface 138. Likewise, the body member 130 has an outlet tube 132 projecting therefrom with a bore 131 and a fixing nose 133 at the end thereof. The nose 133 is shown received in a flexible-walled tube 170. Inside the above-mentioned cylindrical surface 138, the bore 131 opens out into a conical portion 134 which is followed by a cylindrical portion 135 in which a valve seat 136 is received to hold a bead 160 which is captive in a cavity 161. The cavity 161 is defined by the domed surface 117 and by a flat end section 139 of the body member 130.

The cavity 161 has an inlet orifice defined by the end of the bore 111 opeing out therein, and an outlet orifice defined by the valve seat 136. Each of these orifices is of smaller diameter than the bead 160. The seat 136 and the bead 160 cooperate to form a valve having a chosen leakage rate, which rate naturally varies as a function of pressure. The leakage rate is set by forming an orifice 136A which is fully closed by the bead 160, and then in cutting out an extra arc over a portion of the circumference to attain the desired leakage rate. The entire filter assembly is covered in a sheath 150 of soft material.

The valve seat 136 may also be made of soft material. This has the effect of increasing the non-linearity of the filter: the higher the pressure the lower the leakage rate.

In a particular embodiment, the bead 160 is about 2 mm in diameter, and it is made of a bio-implantable material, and preferably a metal, such as stainless steel. Care must be taken to ensure that the bead 160 and the seat 136 co-operate over a relatively limited area in order to avoid the danger of surface tension causing the bead to stick in its closed position. The body members 110 and 130 are made of rigid bio-implantable material such as a polycarbonate or a metal such as stainless steel. The sheath 150 is made of elastic bio-implantable material such as silicone. The tube 170 is likewise preferably made of silicone. Other details of shape and relative proportions can be taken directly from the figure which is drawn to scale, as are FIGS. 3 to 5.

The shape of the seat is adjusted so as to leave a leakage rate of about 20 $cm^3$ per hour under a pressure of 40 cm of water and with the bead in the closed position.

Operation is as follows:

In the event of large changes in flow rate when the patient is lying down, the bead 160 is thrust against the seat 136, thereby opposing any sudden increase in flow rate.

On changing position, and especially when sitting up from a lying position, the beginning of a siphon effect immediately thrusts the bead against its seat 136, thereby increasing resistance to flow and reducing the siphoning. The bead stays on its seat most of the time a patient is sitting or standing.

The operation of a device in accordance with the present invention will be better understood by now referring to FIG. 3 which shows an embodiment in which the filter is incorporated in a pressure threshold valve.

In FIG. 3, a body member 230 corresponds to the body member 130 of FIG. 2, and more generally, items in FIG. 3 which are equivalent to items in FIG. 2 have the same reference numerals, but increased by 100. The tube 270 is fixed to the end of an outlet tube 232 without a nose. The shape of the other body member 210 is somewhat different from the shape of the corresponding body member 110. Its inside surface 212 is conical rather than domed and its orifice 211 is of slightly larger diameter, though still smaller than the diameter of the bead 260. The sheath 250 extends beyond the filter in the upstream direction and defines an upstream chamber 255 having a proximal end piece or inlet tube 280. The tube 280 has a bore 281 and its inside end is equipped with a surrounding lip 282 which clamps a valve member 284 having a slot 285. This arrangement is known and provides a valve which opens at a threshold pressure. The upstream pressure depends on the pressure in the cerebral ventricles. Once it is high enough, the slot 285 opens under the effect of the pressure thereby admitting cephalo-rachidian liquid into the cavity 255 and consequently into the filter situated immediately downstream therefrom.

The function is the same as already described with reference to FIG. 2, and it will be understood that no cephalo-rachidian liquid flows unless there is a sufficient pressure difference across the valve 284 to open its slot 285.

It is immediately apparent that the present invention goes against the previously accepted teaching which consists, as indicated above, in maintaining the intracranial pressure in a prone patient at a constant level regardless of flow rate.

Anti siphon non-return valves have been proposed to avoid siphoning in the sitting and standing positions.

The present invention resides in the addition of a nonlinear, hydraulic filter valve which, in practice, has two states.

When the patient is lying down, any abnormal, long-term increase in intracranial pressure is controlled by the filter which can then pass a high flow rate (e.g. due to hyper secretion of cephalo-rachidian liquid). Conversely, short-term variations in intracranial pressure will take effect normally (e.g. during paradoxical sleep, crying, etc.).

Most of the time the patient is sitting or standing, the bead rests on its seat. This increases the filter impedance and avoids cephalo-rachidian liquid being siphoned and also avoids intracranial pressure dropping below physiological limits.

In practice, it has been observed that filter flow rate varies between 8 $cm^3$ and 25 $cm^3$ per hour for a variation in static pressure across the filter of 5 cm to 50 cm of water.

A second embodiment of the invention using a multiplicity of microbeads is now described with reference to FIGS. 4 and 5.

FIG. 4 shows such a filter on its own for connection in series with a threshold pressure opening valve, either upstream or downstream therefrom. The filter has an upstream or proximal end 380 and a downstream or distal end 390. The proximal end 380 is equipped with a nose 383 for fixing it in a tube. It has a bore 381 which flares out at 389 where the entire end piece 380 flares out at 388. Likewise the distal end 390 has a bore 391 which narrows down from an upstream end 399 inside a tapering portion 398 of the end piece. The filter housing is defined by a generally cylindrical member 365 between the two end pieces. The assembly of the two end pieces and the cylindrical member is surrounded by a sheath 350. Each end of the cylindrical member is countersunk to receive a corresponding filter member 310 or 330 having respective axial perforations 311. The filter members 310 and 330 are glued in place. In a preferred embodiment, the perforations 311 and 331 are slots of width smaller than the diameter of the of the microbeads 360 which are housed in the internal cavity 355 of the filter. The microbeads are not drawn to scale and the number of them appearing in the drawing is less than in practice in order to simplify the drawing.

It has proved possible to choose the diameter and number of the microbeads 360, the volume of the chamber 355, and the size of the perforations through the filters 310 and 330 in such a manner as to obtain the following characteristics:

In the vertical position, the beads collect at the distal filter end and the leakage rate is between 8 $cm^3$ and 25 $cm^3$ per hour for a static pressure difference across the filter of 5 cm to 50 cm of water;

In the horizontal position, since the microbeads occupy only a portion of the cross section of the chamber, they do not constitute an obstacle to the flow of cephalo-rachidian liquid. Typically, the microbeads occupy 50% to 90% of the volume of the chamber in which they are lodged, which leaves plenty of room for the cephalo-rachidian liquid to pass when the filter is horizontal. In a particular embodiment, the microbeads are of between 0.1 mm and 0.6 mm in diameter.

General operation is substantially the same as before:

If there are large variations in flow rate, particularly in a patient who is lying down, the microbeads are swept towards the distal filter 330 and they oppose a sudden increase in flow rate by piling up on one another. This enables the major part of the pressure variations that accompany wakefulness and paradoxical sleep to be maintained;

If there is a change in position, in particular if the patient moves from the lying position to the sitting position, the beginning of a siphon effect immediately entrains the microbeads towards the distal end thereby increasing the resistance to flow and thus reducing the siphoning effect. The microbeads generally remain packed together so long as the patient remains sitting or standing.

Further, any slow and abnormal increase in intracranial pressure is opposed by the average flow rate of cephalorachidian liquid through the filter in accordance with the invention being maintained.

FIG. 5 shows a filter similar to the FIG. 4 filter, but on a smaller scale and incorporated in a pressure threshold valve. The valve is at the lefthand side of the figure and is vary similar to the valve shown in FIG. 3. Corresponding valve items are referenced with numbers beginning with a "4" instead of with a "2". This portion is thus not described a second time. The righthand end of FIG. 5 shows the main filter items already shown in FIG. 4, in particular an outer casing 490 housing both a proximal filter 410 and a distal filter 430 which are glued to the inside of the casing and held apart by a spacer 465. As before, the filters 410 and 430 have perforations 411 and 431 which are advantageously constituted by slots. A multitude of microbeads 460 are lodged inside the chamber 455 defined by said filter. The diameter of the microbeads is greater than the width of the perforations 411 and 431. The other characteristics of the filter are determined as indicated above.

In a particular embodiment of the type shown in FIGS. 4 and 5, the microbeads are made of silicone coated glass. The parts which are hatched with lines sloping down from left to right are made of a hard bio-implantable plastic such as polycarabonate. The parts which are hatched with lines sloping up from left to right are made of soft bio-implantable material such as silicone. The stippled parts are tubes or threshold valves 484, 284 made of silicone.

Although the devices as described above with reference to FIGS. 2 to 5 give excellent results on their own, they are advantageously used in combination with a special catheter as shown in FIG. 6.

In this figure, O represents skull bone lying over the dura mater DM, then the arachnoid, and then subarachnoid spaces ESA. These retain the brain mass C by means of villosities, and the inside of the brain mass is delimited by a cerebral ventricle CV. A normal catheter simply passes through a hole in the skull O to reach the cerebral ventricles, where its proximal end 20 has perforations 21 to 25 for evacuating cephalo-rachidian liquid. The improved catheter has a stop member 30 which is lodged between the skull and the dura mater, and which is immediately followed by intermediate orifices 40. These orifices serve to remove the liquid filling the subarachnoid spaces so as to avoid inverting the pressure gradient across the brain mass C. The difference in total orifice area between the end holes 21 to 25 and the intermediate orifices 40 must be sufficient for the action of pumping the cephalorachidian liquid to take effect initially on the sub-arachnoid spaces, and only subsequently on the cerebral ventricles.

It has been indicated above that a filter in accordance with the invention reduces, in particular, the effects of siphoning when the patient changes position. The catheter described above is advantageously combined with the filter to ensure that an undesirable pressure difference does not appear across the two faces of the brain mass C. The risk of subdural hematoma is thus further reduced.

We claim:

1. A hydrocephaly treatment device comprising an intracranial catheter connected to a tube fitted with a first valve for diverting the flow of cephalo-rachidian liquid to one or more cavities in the organism capable of absorbing said liquid, the improvement wherein a hydraulic filter of non-linear variable impedance is connected in said tube in series with said valve, said filter comprising at least one bead and one outlet orifice for the cephalo-rachidian liquid, said outlet orifice substantially cooperating with said at least one bead to form a seat of a leakage rate valve the leakage rate of which varies as a function of pressure, said filter maintaining an average flow rate of the cephalo-rachidian liquid defined by said leakage rate close to the physiological flow rate, thereby permitting the intracranial pressure to vary in the short term over a characteristic period of about one second, while preventing said pressure from varying in the long term over a characteristic period of about one minute.

2. A device according to claim 1, wherein said hydraulic filter is located in a portion of the path of said tube, said portion being in substantially parallel relationship with the longitudinal axis of said organism, wherein said at least one bead is movably retained in the path of the cephalo-rachidian liquid between a filter inlet orifice and the filter outlet orifice, said orifices being dimensioned to prevent said at least one bead passing therethrough.

3. A device according to claim 2, wherein said leakage flow rate is about 8 $cm^3$ to 30 $cm^3$ per hour for a static pressure difference across said filter of 5 cm to 40 cm of water.

4. A device according to claim 2, wherein said hydraulic filter is incorporated in a common structure with said first valve, and wherein said first valve is a non-return valve which opens at a fixed threshold pressure.

5. A device according to claim 2, wherein said filter includes one bead only, and wherein said outlet orifice constitutes a bead-receiving seat for said leakage flow rate valve.

6. A device according to claim 5, wherein the diameter of said bead is about 2 mm.

7. A device according to claim 2, wherein said filter includes a large number of microbeads, said filter inlet and outlet orifices being in the form of respective filters having perforations of width smaller than the diameter of said microbeads.

8. A device according to claim 11, wherein said microbeads are of a diameter lying in the range 0.1 mm to 0.6 mm.

9. A device according to claim 11, wherein said microbeads are housed in a chamber betwen said filter inlet and outlet orifices, and wherein said microbeads occupy 50% to 90% of the internal volume of said chamber.

10. A device according to claim 1, wherein said intracranial catheter has a free end fitted with orifices for communication with the cerebral ventricles, and wherein said catheter further includes a stop member located a predetermined distance from said free end together with one or more intermediate orifices located adjacent to said stop member and on the free end side thereof, said intermediate orifices being for communication with the sub-arachnoid spaces of the cranial cavity, thereby making it possible to avoid inverting the pressure gradient between the ventricular cavities and the periphery of the cerebral parenchyma.

11. A hydrocephaly treatment device comprising an intracranial catheter connected to a tube fitted with a first valve for diverting the flow of cephalo-rachidian liquid to one or more cavities in the organism capable of absorbing said liquid, the improvement wherein a hydraulic filter of non-linear variable impedance is connected in said tube in series with said valve in a portion of the path of said tube in substantially parallel relationship with the longitudinal axis of said organism, said filter comprising a plurality of micro-beads, an inlet orifice and an outlet orifice for the cephalo-rachidian liquid, the orifices in the form of filters having perforations of width smaller than the diameter of the micro-beads to prevent said micro-beads from passing therethrough, said outlet orifice substantially cooperating with said micro-beads to form a leakage rate valve, the leakage rate of which varies as a function of pressure, said filter maintaining an average flow rate of the cephalo-rachidian liquid defined by said leakage rate, close to the physiological flow rate, thereby permitting the intracranial pressure to vary in the short term over a characteristic period of about one second, while preventing said pressure from varying in the long term over a characteristic period of about one minute.

12. A device according to claim 11, wherein said intracranial catheter has a free end fitted with orifices for communication with the cerebral ventricles, and wherein said catheter further includes a stop member located a predetermined distance from said free end together with one or more intermediate orifices located adjacent said stop member and on the free end side thereof, said intermediate orifices being for communication with the sub-arachnoid spaces of the cranial cavity, thereby making it possible to avoid inverting the pressure gradient between the ventricular cavities and the periphery of the cerebral parenchyma.

* * * * *